(12) United States Patent
Griesbach, III

(10) Patent No.: US 7,409,953 B2
(45) Date of Patent: Aug. 12, 2008

(54) SURGICAL DRAPE HAVING AN EXPANDABLE MEMBER

(75) Inventor: Henry L. Griesbach, III, Clarkston, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 533 days.

(21) Appl. No.: 10/737,163

(22) Filed: Dec. 16, 2003

(65) Prior Publication Data

US 2005/0126577 A1   Jun. 16, 2005

(51) Int. Cl.
*A61F 5/37* (2006.01)

(52) U.S. Cl. ...................................................... 128/849

(58) Field of Classification Search ................. 128/849, 128/118.1, 865, 855, 853, 831, 850, 852, 128/854; 602/41; 359/510
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,763,857 A * | 10/1973 | Schrading | 128/853 |
| 3,770,119 A | 11/1973 | Hultberg | |
| 3,802,817 A | 4/1974 | Matsuki et al. | |
| 3,849,241 A | 11/1974 | Butin et al. | |
| 3,855,046 A | 12/1974 | Hansen et al. | |
| 3,863,343 A | 2/1975 | Malmin | |
| 3,921,627 A * | 11/1975 | Wilson et al. | 128/853 |
| 4,340,563 A | 7/1982 | Appel et al. | |
| 4,379,192 A | 4/1983 | Wahlquist et al. | |
| 4,466,430 A | 8/1984 | Shultz | |
| 4,570,628 A * | 2/1986 | Neal | 128/853 |
| 4,598,458 A | 7/1986 | McAllester | |
| 4,974,604 A | 12/1990 | Morris | |
| 5,005,590 A | 4/1991 | Eldridge | |
| 5,097,963 A | 3/1992 | Chernosky et al. | |
| 5,170,804 A | 12/1992 | Glassman | |
| 5,195,538 A | 3/1993 | Eldridge, Jr. et al. | |
| 5,358,111 A | 10/1994 | Greenberg | |
| 5,418,045 A | 5/1995 | Pike et al. | |

(Continued)

FOREIGN PATENT DOCUMENTS

DE    2 522 667    2/1976

(Continued)

OTHER PUBLICATIONS

U.S. Appl. No. 10/323,305, (KCX-629) filed Dec. 18, 2002.

(Continued)

*Primary Examiner*—Justine R Yu
*Assistant Examiner*—Shumaya B Ali
(74) *Attorney, Agent, or Firm*—Dority & Manning, P.A.

(57) ABSTRACT

A surgical drape for use during surgery includes a sheet that is configured for covering at least a portion of a patient. The sheet has a top surface and a bottom surface that is opposite from the top surface. An expandable member is carried by the sheet. The expandable member has an unexpanded orientation and an expanded orientation. The expandable member forms a raised portion when in the expanded orientation.

43 Claims, 14 Drawing Sheets

U.S. PATENT DOCUMENTS

| | | | |
|---|---|---|---|
| 5,464,024 A * | 11/1995 | Mills et al. | 128/49 |
| 5,503,163 A | 4/1996 | Boyd | |
| 5,540,979 A | 7/1996 | Yahiaoui et al. | |
| 5,558,654 A | 9/1996 | Hardy | |
| 5,632,284 A | 5/1997 | Graether | |
| 5,941,907 A * | 8/1999 | Augustine | 607/104 |
| 6,003,328 A | 12/1999 | Faries, Jr. et al. | |
| 6,055,987 A | 5/2000 | Griesbach et al. | |
| 6,070,586 A | 6/2000 | Harroll et al. | |
| 6,142,152 A | 11/2000 | Gawarecki | |
| 6,203,567 B1 | 3/2001 | Augustine | |
| 6,269,815 B1 | 8/2001 | Jascomb | |
| 6,314,958 B1 | 11/2001 | Harroll et al. | |
| 6,863,071 B2 * | 3/2005 | Annett et al. | 128/849 |
| 7,096,871 B2 | 8/2006 | Lee et al. | |
| 2004/0149291 A1 * | 8/2004 | Lee et al. | 128/849 |

FOREIGN PATENT DOCUMENTS

| | | |
|---|---|---|
| FR | 2775184 A | 8/1999 |
| WO | WO 0241800 | 5/2002 |
| WO | WO 2004021912 A1 | 3/2004 |

OTHER PUBLICATIONS

Search Report and Written Opinion for PCT/US2004/016931, Nov. 22, 2004.

U.S. Appl. No. 10/286,388, (KCX-613A) filed Nov. 1, 2002.

U.S. Appl. No. 10/326,913, (KCX-628) filed Dec. 20, 2002.

U.S. Appl. No. 10/323,305, (KCX-629) filed Dec. 18, 2002.

* cited by examiner

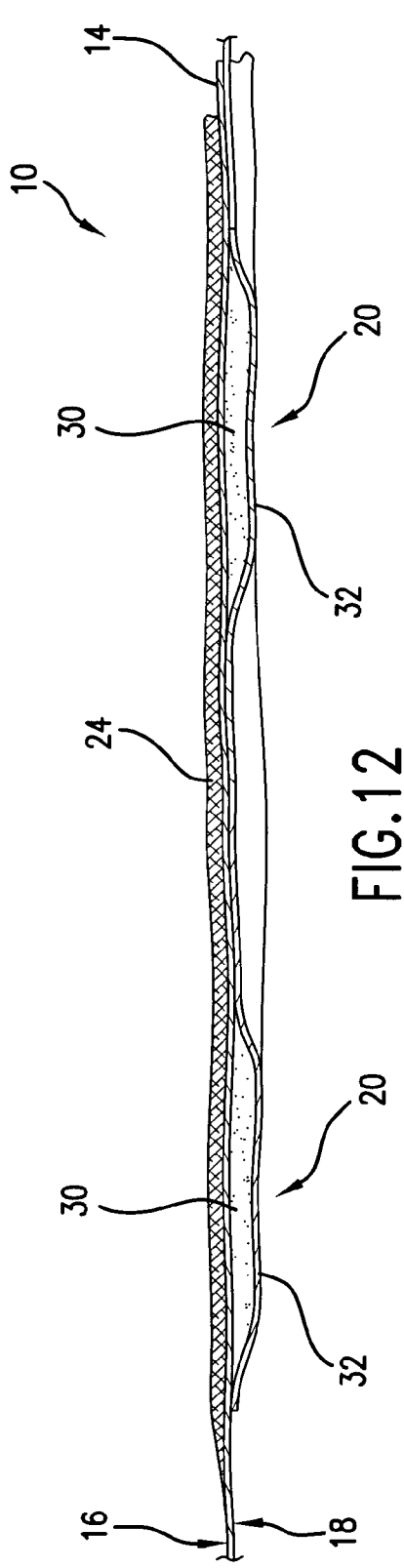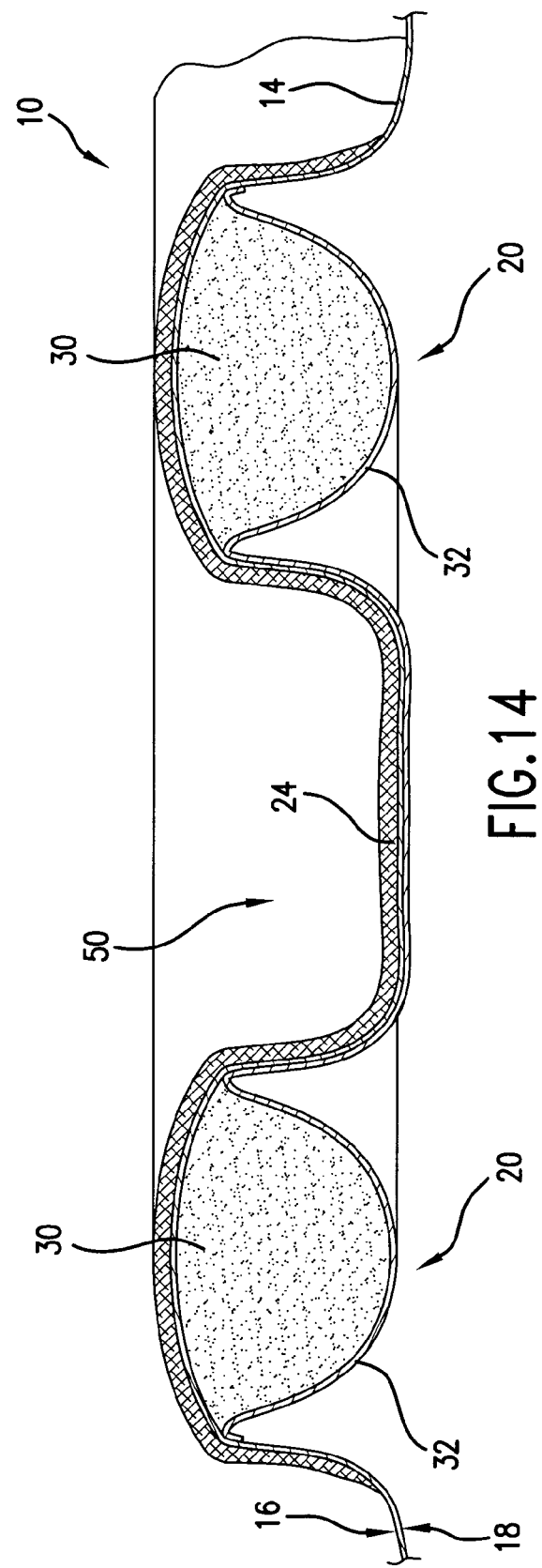

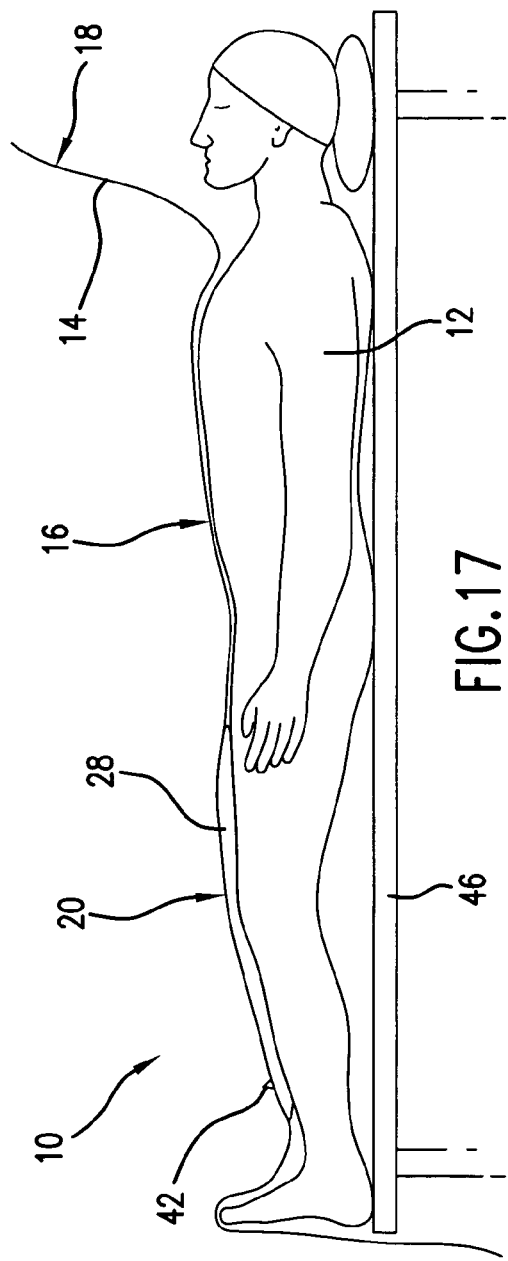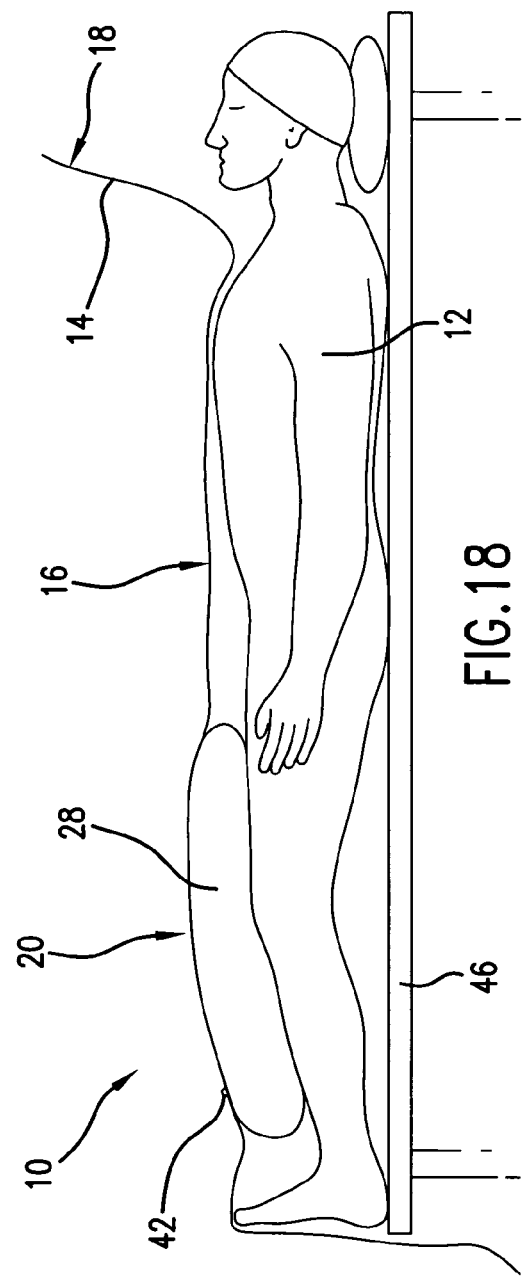

SURGICAL DRAPE HAVING AN EXPANDABLE MEMBER

BACKGROUND

Various types of surgical drapes have been used to keep a surgical site on a patient sterile during a surgical procedure. Disposable drapes are sometimes employed and typically include a nonwoven paper or fabric that forms a substantial part of the disposable drape. A reinforcement area is often placed around a fenestration to provide structural strength and/or to absorb bodily fluids from the surgical site.

Certain surgical procedures involve large amounts of fluid, for example blood or saline irrigation fluid, at the point of surgery. In order to remove unwanted fluid, towels, suctioning devices, surgical sponges, and other fluid management devices are sometimes employed. Additionally, surgical drapes are sometimes provided with a plastic trough, pouch, or other device, which is configured to allow fluid to be transported from the point of surgery to a more remote area of the surgical drape. Wherein, the excess fluid may be contained within a pouch or other member capable of containing the excess fluid, and may be subsequently disposed.

Surgical drapes have also been designed in order to maintain surgical instruments thereon that are used during a surgical procedure. For instance, a plurality of binding strips of material may be attached to the upper surface of the drape and include a hook and loop type fastener in order to engage and retain one or more surgical devices. Designs of this type require the surgeon to manipulate the device in order to remove and attach the surgical instruments therefrom.

The present invention provides for an improved surgical drape that allows for channeling of fluid on the surgical drape, retention or collection of fluid, securement of instruments on the surgical drape, cushioning for the patient and/or healthcare provider during surgery, and/or helping to define inlet openings in pouches, pockets, sleeves, and the like.

SUMMARY

Various features and advantages of the invention will be set forth in part in the following description, or may be obvious from the description.

The present invention provides a surgical drape that includes a sheet configured for covering at least a portion of a patient during surgery. The sheet has a top surface and a bottom surface opposite from one another. An expandable member is carried by the sheet and has both an unexpanded orientation and an expanded orientation. The expandable member forms a raised portion on the drape when the expandable member is in the expanded orientation.

The expandable member provides various beneficial features to the surgical drape. For instance, the expandable member may act as a cushioning member to prevent injury or unwanted forces from contacting the patient and/or healthcare provider. The expandable member may act as a diverting member to divert the flow of fluid that contacts the sheet, or as a fluid retention member to retain fluid that contacts the sheet. The expandable member may also aid in optimally positioning fluid collection components attached to the drape. Additionally, the expandable member may act as an instrument holder that is configured for receiving surgical instruments and may aid in positioning the drape itself on the patient.

The expandable member may be configured differently in accordance with various exemplary embodiments of the present invention. For instance, the expandable member may be a chamber that is inflatable from the unexpanded orientation to the expanded orientation by a fluid, for example air. Alternatively, the expandable member may be open cell foam that is reversibly collapsed and sealed in an appropriately sized collapsed constraining chamber, for example an envelope, when in the unexpanded orientation. Breaking or opening the collapsed chamber causes the chamber's interior to contact ambient pressure air which removes the constraining forces on the open cell foam such that the open cell foam then expands into the expanded orientation.

The expandable member may be oriented on the sheet in a number of various configurations. The expandable member may be located on the top surface of the sheet, or on the bottom surface of the sheet. The expandable member may be integrally formed with the sheet, or may be a separate component that is attached to the sheet. The sheet may include a fenestration and have a fabric that surrounds the fenestration. In this instance, the expandable member may be either spaced from the fabric, or carried by the fabric. The fabric may absorb fluid; it may be fluid repellent, or a combination of both.

The expandable member may also provide for means to define an inlet opening for sleeves, pockets, pouches, and the like. The expandable member may, in certain exemplary embodiments, be configured so that when placed into the expanded orientation the expandable member helps define an inlet opening of a fluid retaining pouch.

BRIEF DESCRIPTION OF THE DRAWINGS

A full and enabling disclosure of the present subject matter, including the best mode thereof, directed to one of ordinary skill in the art, is set forth in this specification, which makes reference to the appended figures, in which:

FIG. 12 is a cross-sectional view taken along line 12-12 of FIG. 11.

FIG. 14 is a cross-sectional view taken along line 14-14 of FIG. 13.

FIG. 17 is a side view of an exemplary embodiment of a surgical drape in accordance with the present invention. The expandable member is in the unexpanded orientation.

FIG. 18 is a side view of the surgical drape of FIG. 17 in which the expandable member is in the expanded orientation.

Figure 1:
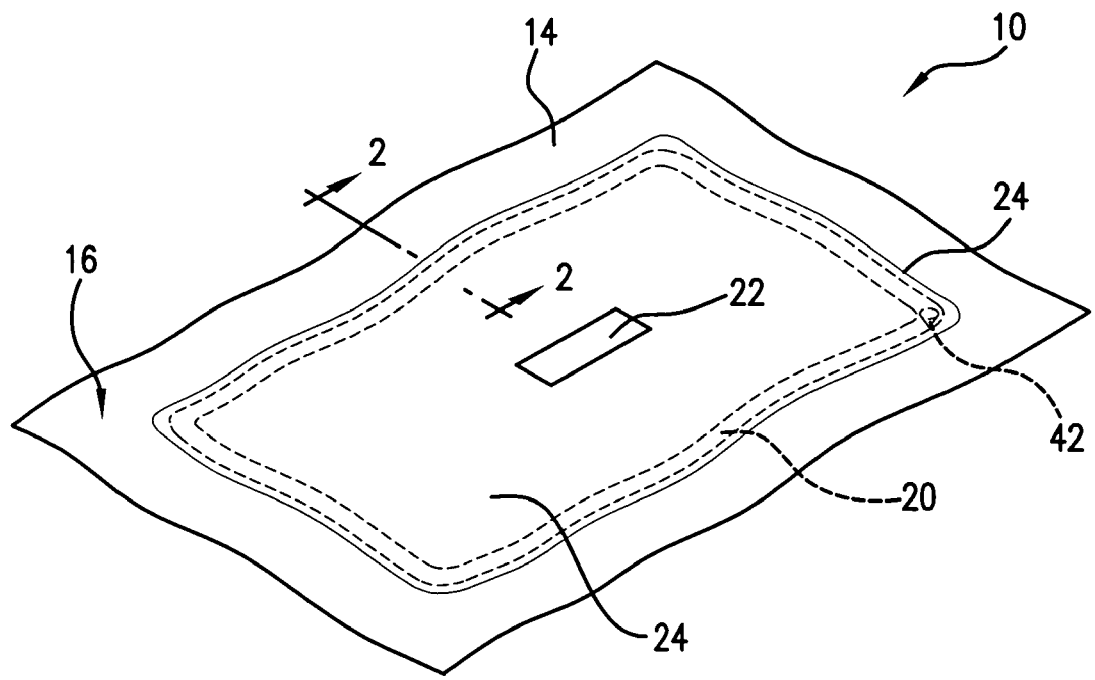
FIG. 1 is a perspective view of a surgical drape in accordance with one exemplary embodiment of the present invention with an expandable member in an unexpanded orientation.

Repeat use of reference characters throughout the present specification and appended drawings is intended to represent same or analogous features or elements of the invention.

DETAILED DESCRIPTION

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

The present invention is not limited to the numerical ranges and limits discussed herein. For example, a range of from about 100 to about 200 also includes ranges from about 110 to about 190, about 140 to about 160, and from 131 to 145. As a further example, a numerical limit of less than about 10 also includes a numerical limit of less than about 7, less than about 5, and less than about 3.

Referring to FIG. 1 in general, the present invention provides for a surgical drape 10 that has a sheet 14 for use in covering at least a portion of a patient during a medical procedure. An expandable member 20 is carried by the sheet 14 and may be configured in both an unexpanded orientation and an expanded orientation. The expandable member 20 shapes the surgical drape 10 so that fluid that contacts the surgical drape 10 can be diverted into a desired location and/or retained on the surgical drape 10. The expandable member 20 also is capable of shaping the surgical drape 10 so that an area is formed in which surgical instruments may be retained on the surgical drape 10. Additionally, the expandable member 20 may act as a cushioning member in order to protect the patient and/or healthcare provider from unwanted forces or injury.

The surgical drape 10 formed in accordance with the present invention can generally possess any variety of size or shape, depending on the particular use of the surgical drape 10 and its desired properties. For example, the surgical drape 10 may be configured as described in U.S. Pat. No. 6,055,987 issued to Griesbach, et al., which is incorporated by reference herein in its entirety for all purposes. In one exemplary embodiment of the present invention, the sheet 14 is 193 cm by 305 cm (76 inches by 120 inches) and is made of polyolefinic spunbond and meltblown layers. A fabric 24 may be incorporated into this exemplary embodiment and be for example, 65 cm by 100 cm (25.6 inches by 39.4 inches).

Figure 2:
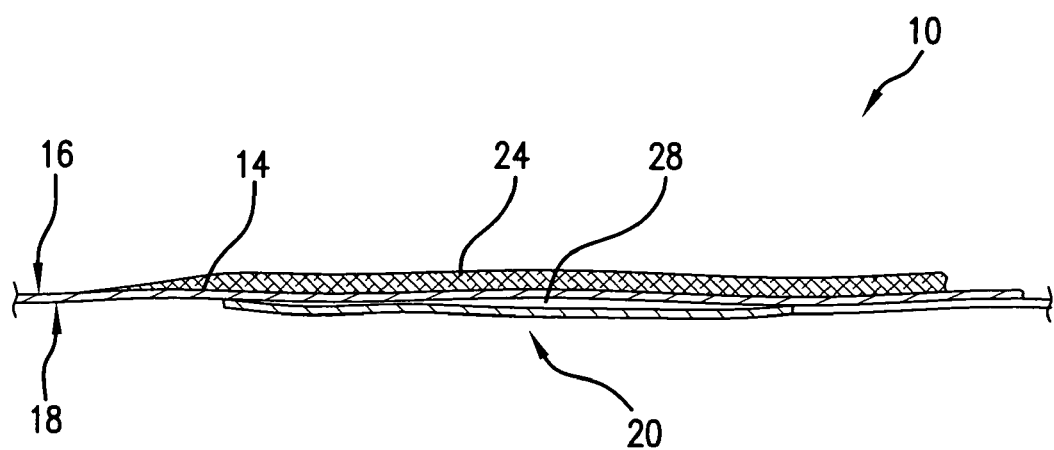
FIG. 2 is a cross-sectional view in along line 2-2 of FIG. 1.

FIG. 1 shows a perspective view of the surgical drape 10 having a sheet 14 that defines a fenestration 22 (an opening through the surgical drape 10). The fenestration 22 may be of any size or shape. Additionally, the fabric 24 may completely surround each side of the fenestration 22, or may be placed adjacent to only one, two, or three sides of the fenestration 22. For instance, in accordance with one exemplary embodiment of the present invention and depicted in FIG. 1, the fenestration 22 is a 10 cm by 30.5 cm (3.94 inches by 12 inches) rectangular opening. The fabric 24 is incorporated into the sheet 14 and surrounds the fenestration 22. In this instance, the fabric 24 is connected to a top surface 16 of the sheet 14. The expandable member 20 is a separate component that is attached to a bottom surface 18 of the sheet 14. The expandable member 20 is bonded on either side to the sheet 14 (as seen in FIG. 2) and extends completely around the fenestration 22. As such, the expandable member 20 defines a single chamber 28 that circumvents the fenestration 22.

Figure 3:
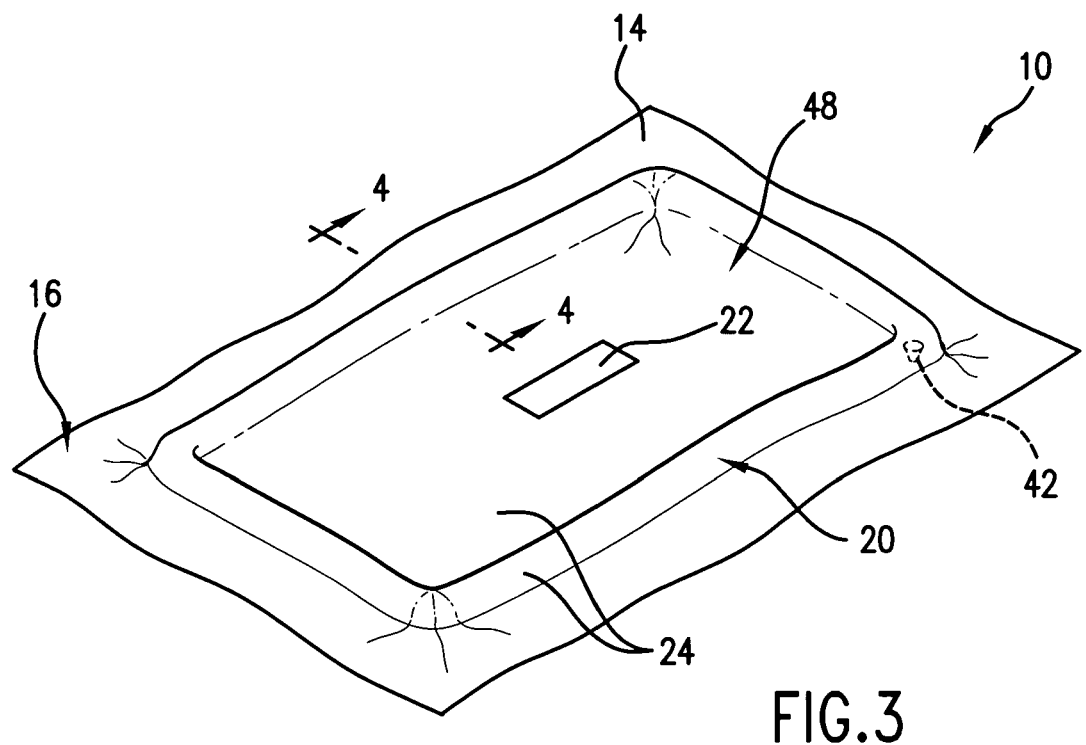
FIG. 3 is a perspective view of the surgical drape of FIG. 1 in which the expandable member is placed into the expanded orientation.
Figure 4:
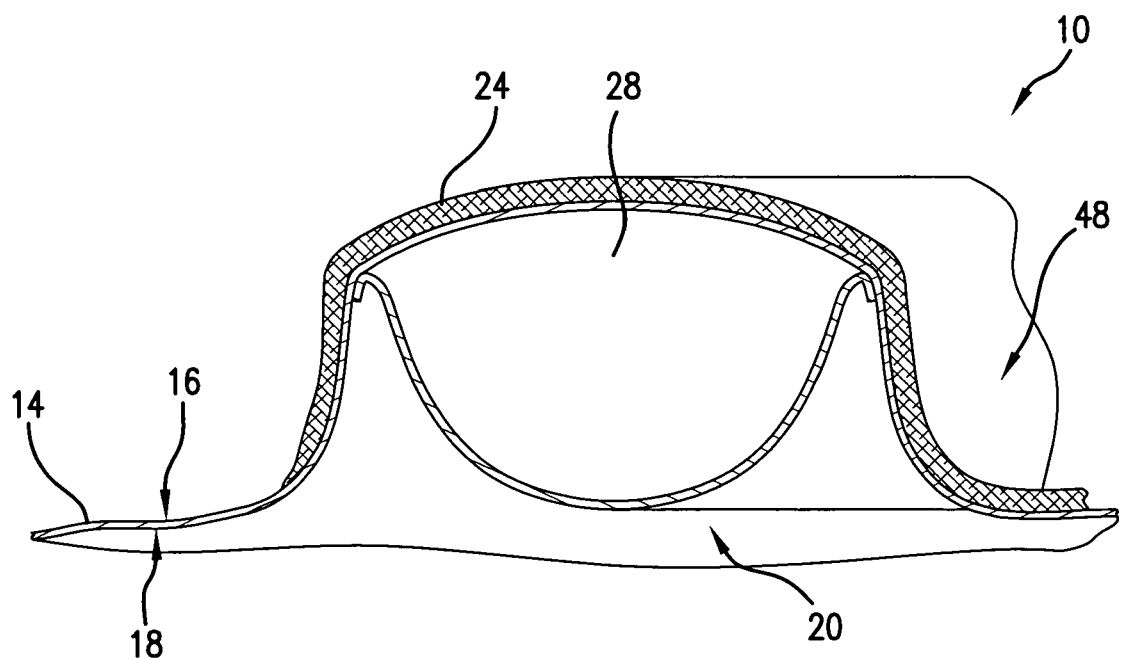
FIG. 4 is a cross-sectional view taken along line 4-4 of FIG. 3.
Figure 5:
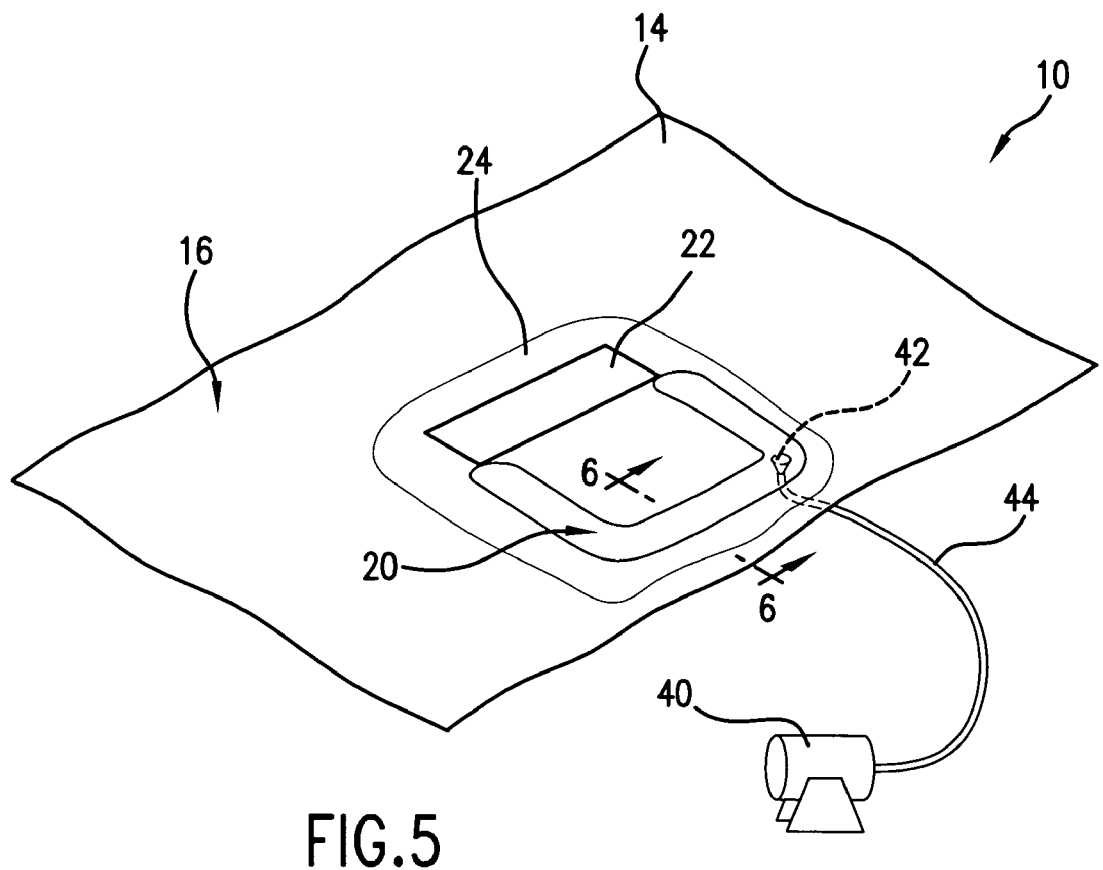
FIG. 5 is a perspective view of a surgical drape in accordance with one exemplary embodiment of the present invention. The expandable member is in the unexpanded orientation.

FIGS. 3 and 4 show the surgical drape 10 of FIGS. 1 and 2 when the expandable member 20 is placed into the expanded orientation. In this regard, the expandable member 20 is provided with a port 42 into which air or other fluid may be directed. Doing so will cause the chamber 28 to expand. Expansion of the chamber 28 will cause a subsequent change in the contour of the sheet 14 as can be seen upon comparison of FIG. 1 and FIG. 3. In this regard, expansion of the chamber 28 causes the sheet 14 to rise upwards such that a valley 48 is defined on the top surface 16 to form a recedtacle for fluid. Fluid from a surgical procedure may be contained in the valley 48 and prevented from running off of the sheet 14. Additionally, the valley 48 may be used in order to help keep surgical instruments (FIG. 23) from sliding or falling off of the sheet 14. Additionally, the fluid filled chamber 28 may help to cushion the patient 12 and/or the healthcare provider from various forces. The expandable member 20 may alternatively be configured so that when in the expanded orientation, the contour of the surgical drape 10 is changed from a wavy contour to a flat contour.

With reference to FIGS. 2 and 4, the chamber 28 is shown as being defined by both the expandable member 20 and the bottom surface 18 of the sheet 14. It is to be understood that the expandable member 20 may be alternatively made of either chambers and/or elements and may be made of any number of chambers and/or elements. The surgical drape 10 may additionally be configured so that the chamber 28 is defined entirely by the expandable member 20. This type of configuration (not shown in FIGS. 1-4) eliminates the need of having a pair of fluid seals along the entire length of the expandable member 20 (as would be the case shown in FIGS. 1-4). In this instance, two layers of impervious film that are attached to one another, or one layer of impervious film define the chamber 28.

The expandable member 20 may be incorporated into any portion of the surgical drape 10, for instance the sheet 14 and/or the fabric 24, or may be attached to either the top surface 16 or bottom surface 18 of the sheet 14. Further, the expandable member 20 may be located between the fabric 24 and sheet 14. The expandable member 20 may include stretchable and/or non-stretchable components or material.

The expandable member 20 may be positioned, shaped, and configured in the surgical drape 10 in a variety of manners in accordance with other exemplary embodiments of the present invention. For instance, FIGS. 5 through 8 show an exemplary embodiment wherein the expandable member 20 is in the shape of a horseshoe and is located proximate to the fenestration 22. The expandable member 20 is incorporated on the top surface 16 of the sheet 14. In the expanded orientation shown in FIG. 7, the expandable member 20 is open on one end, but still provides for an area in which fluid or surgical instruments 34 may be directed or retained.

Figure 6:
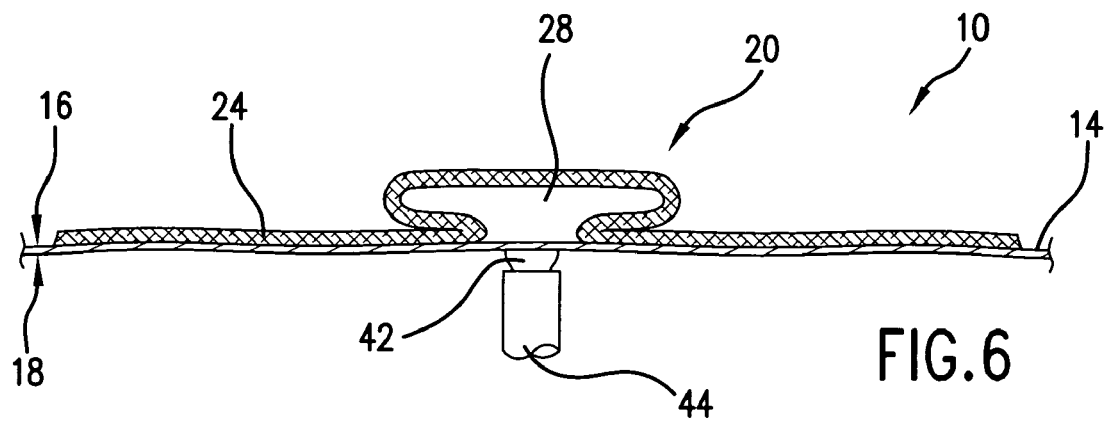
FIG. 6 is a cross-sectional view taken along line 6-6 of FIG. 5.
Figure 7:
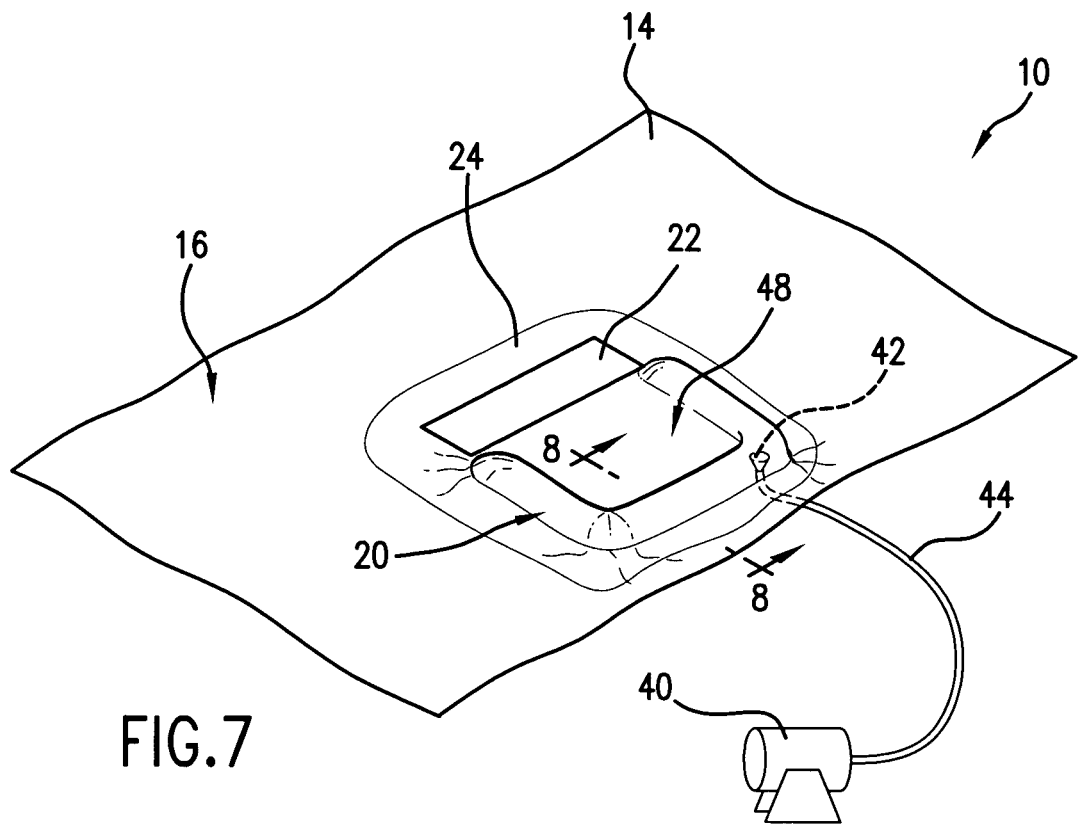
FIG. 7 is a perspective view of the surgical drape of FIG. 5 in which the expandable member is placed into the expanded orientation.
Figure 8:
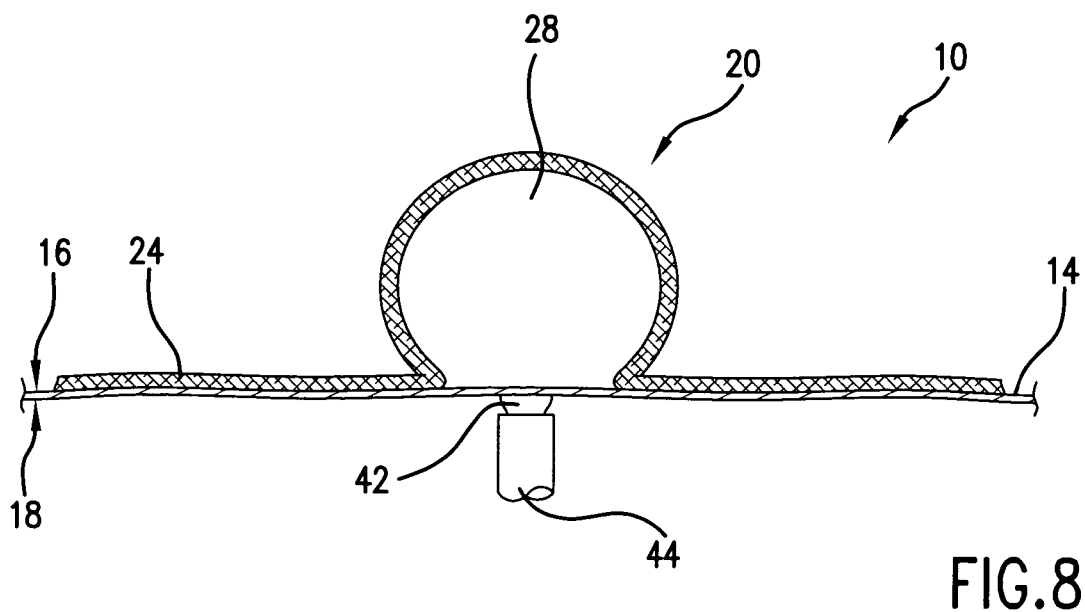
FIG. 8 is a cross-sectional view taken along line 8-8 of FIG. 7.

As can be seen in FIGS. 6 and 8, the expandable member 20 is integrally formed with the sheet 14. Here, the fabric 24, which is part of the sheet 14, is shaped in order to define the chamber 28. Expansion of the chamber 28 causes a portion of the fabric 24 defining the chamber 28 to expand outwards.

It is to be understood that in accordance with other exemplary embodiments, the fabric 24 may not be present. In this instance, the expandable member 20 may be integrally formed by the sheet 14 without the aid of additional material. It is to be understood that the expandable member 20 and the chamber 28 may be of any cross-sectional shape, in either the expanded or unexpanded orientations, and the present invention is not limited to the specific cross-sectional shapes shown in the drawings.

The expandable member 20 shown in FIGS. 5 through 8 is expanded by the insertion of a fluid through the port 42. For example, an air pump 40 may be used in order to insert air into the expandable member 20 through a fluid line 44 connected to the port 42. The air pump 40 may be either power operated or hand operated. Additionally, it is to be understood that any type of fluid may be inserted into the expandable member 20 in order to move the expandable member 20 from the unexpanded to the expanded orientations, and the present invention is not limited to configurations in which only air is used. Additionally, the present invention includes various exemplary embodiments where an alternate device is used in order to insert fluid into the expandable member 20. For example, a syringe-type device may be connected to the expandable member 20 and fluid may be directed therein in order to affect expansion of the expandable member 20. Alternatively, a compressed gas in a cylinder, such as a 12 gm disposable $CO_2$ cylinder, may be used in order to inflate the chamber 28.

The expandable member 20 may be configured so that the chamber 28 is airtight, or may allow for some degree of air to escape. In this manner, the expandable member 20 may be placed into the expanded orientation and sufficient air may be present to keep the expandable member 20 in the expanded orientation during the surgical procedure. Once the surgical procedure has been completed, air may leak from the chamber 28 thus reorienting the expandable member 20 into the unexpanded orientation after some amount of time has passed.

The expandable member 20 may be configured so that the expandable member 20 is capable of being repeatably varied between the unexpanded orientation and the expanded orientation. For instance, after expansion, the port 42 may be opened in order to allow fluid to be evacuated from the chamber 28. When expansion is again desired, fluid may be reintroduced into the chamber 28 in order to place the expandable member 20 into an expanded orientation.

Although shown as having one chamber 28, it is to be understood that in accordance with other exemplary embodiments, any number of chambers 28 may be employed. Additionally, the chambers 28 may be capable of being separately inflated into the expanded orientation so that various contours may be formed on the sheet 14. As such, any number of expandable members 20 may be included with the surgical drape 10, and may be of any size or shape.

When located on the bottom surface 18 of the sheet 14, expansion of the expandable member 20 causes a portion of the sheet 14 to move upward, hence modifying the contour of the sheet 14. When positioned on the top surface 16, expansion of the expandable member 20 may cause an overall change in the contour of the surgical drape 10, but with a minimal degree of change to the sheet 14. When incorporated into the sheet 14 and/or fabric 24, expansion of the expandable member 20 may cause a change in the contour in the sheet 14 and may cause movement in one or more directions of the sheet 14.

Figure 9:
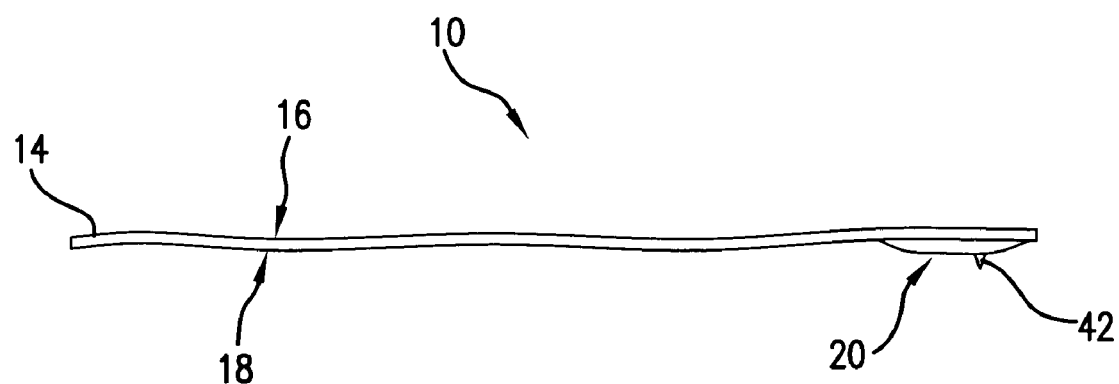
FIG. 9 is a side view of an exemplary embodiment of a surgical drape in accordance with the present invention. The expandable member is in the unexpanded orientation.
Figure 10:
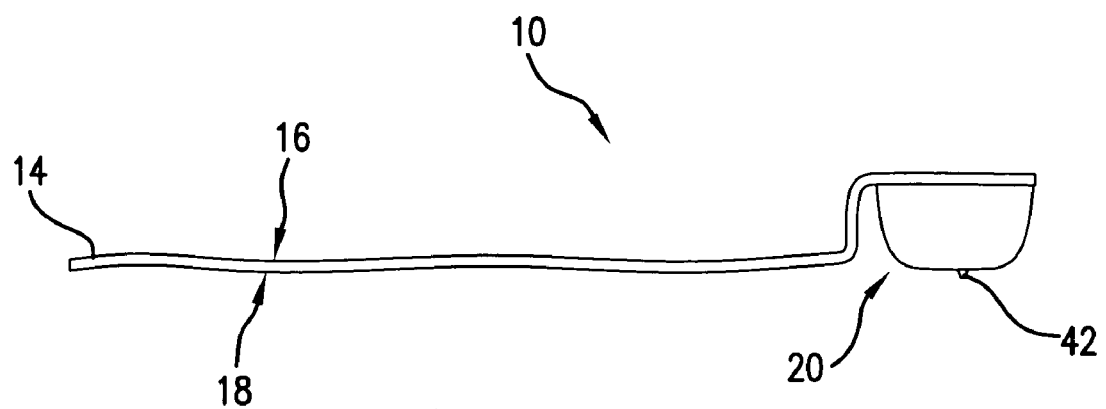
FIG. 10 is a side view of the surgical drape shown in FIG. 9 in which the expandable member is in the expanded orientation.
Figure 11:
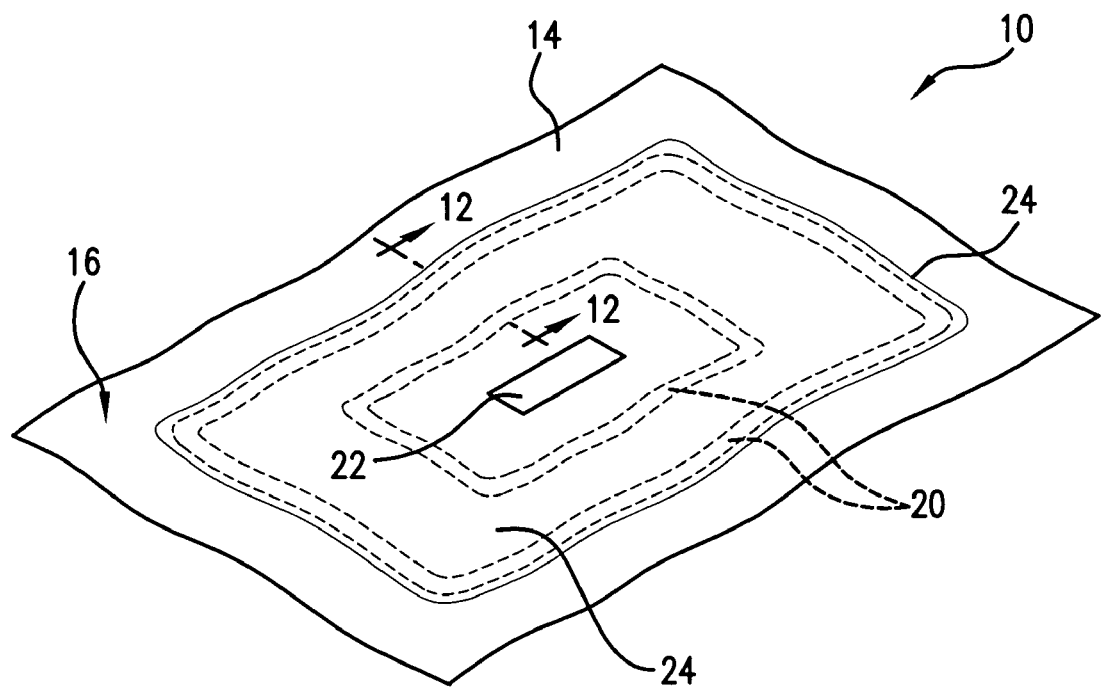
FIG. 11 is a perspective view of a surgical drape in accordance with one exemplary embodiment of the present invention. The expandable members are shown in the unexpanded orientation.

FIGS. 9 and 10 show an alternative exemplary embodiment in which the expandable member 20 is attached to the bottom surface 18 and towards one end of the sheet 14. The raised portion shown in FIG. 10 is capable of acting as a cushioning member, preventing surgical instruments 34 from sliding off of the surgical drape 10, and may help direct fluid on the top surface 16 of the surgical drape 10. Expansion of the expandable member 20 may move the top surface 16 upwards a distance of, for example: from 7.6 to 15 cm (3 to 6 inches).

An alternative exemplary embodiment of the surgical drape 10 is shown in FIGS. 11 through 14. Here, the expandable member 20 includes open cell foam 30 that is constrained in a reversibly collapsed form in an envelope 32 when in the unexpanded orientation shown in FIGS. 11 and 12. The open cell foam 30 may be compressed and then covered by the envelope 32 such that a substantial portion of the air is removed from the open cell foam 30. At this point, the envelope 32 may be hermetically sealed in order to constrain the open cell foam 30 into a compressed, unexpanded orientation. Exposure of the open cell foam 30 to air may, in one exemplary embodiment, cause an upward expansion of 1.3 cm (0.5 inch).

The envelope 32 may be punctured or otherwise opened in order to connect the interior of the envelope 32 and the open cell foam 30 to ambient pressure air. In this regard, the envelope 32 may be provided with a tab (not shown) or similar device which can be pulled in order to break open the envelope 32.

Figure 13:
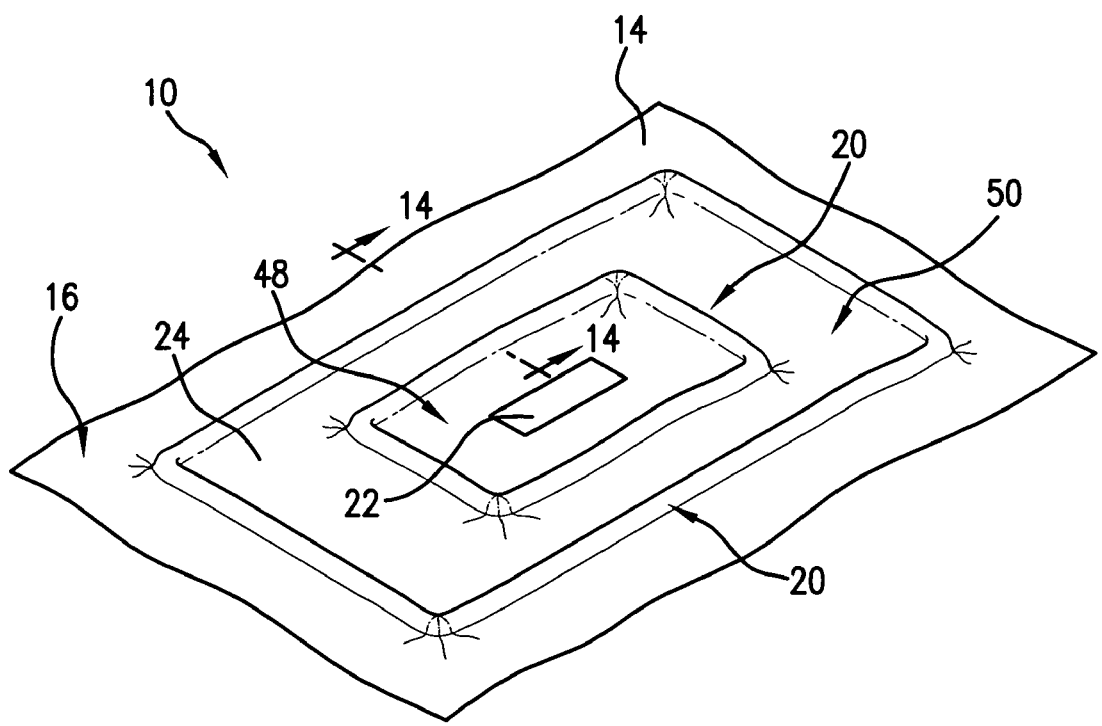
FIG. 13 is a perspective view of the surgical drape of FIG. 11. The expandable member is in the expanded orientation.

Exposing the open cell foam 30 to ambient pressure air will allow the open cell foam 30 to expand, hence reorienting the expandable member 20 from the unexpanded orientation to the expanded orientation shown in FIGS. 13 and 14. Each expandable member 20 is shown as being two pieces of open cell foam 30 which, in the expanded orientation, forms the valley 48 and a second valley 50. Each expandable member 20 may be configured so that each piece of the open cell foam 30 is capable of expanding independently of the other. In this manner, the healthcare provider may expand one piece of open cell foam 30 while keeping the other piece of open cell foam 30 unexpanded. This allows for a greater degree of freedom in reorienting the surgical drape 10 into desired configurations depending upon the particular needs of a surgical procedure. Alternatively, each piece of open cell foam 30 may be expanded simultaneously in accordance with other exemplary embodiments of the present invention. The expandable members 20 may allow for the valley 48 to be used for fluid retention, and for the second valley 50 to be used for the retention of the surgical instruments 34.

The expandable member 20 may include an envelope 32 measuring about 3.8 cm (1.5 inches) by 53.3 cm (21 inches) and the open cell foam 30 measuring about 1.9 cm (0.75 inches) by 1.6 cm (0.625 inches) by 45.7 cm (18 inches). Both the envelope 32 and the open cell foam 30 may be compressed and sealed to form a relatively flat tube that has a thickness of about 0.3 cm (0.125 inches).

Figure 15:
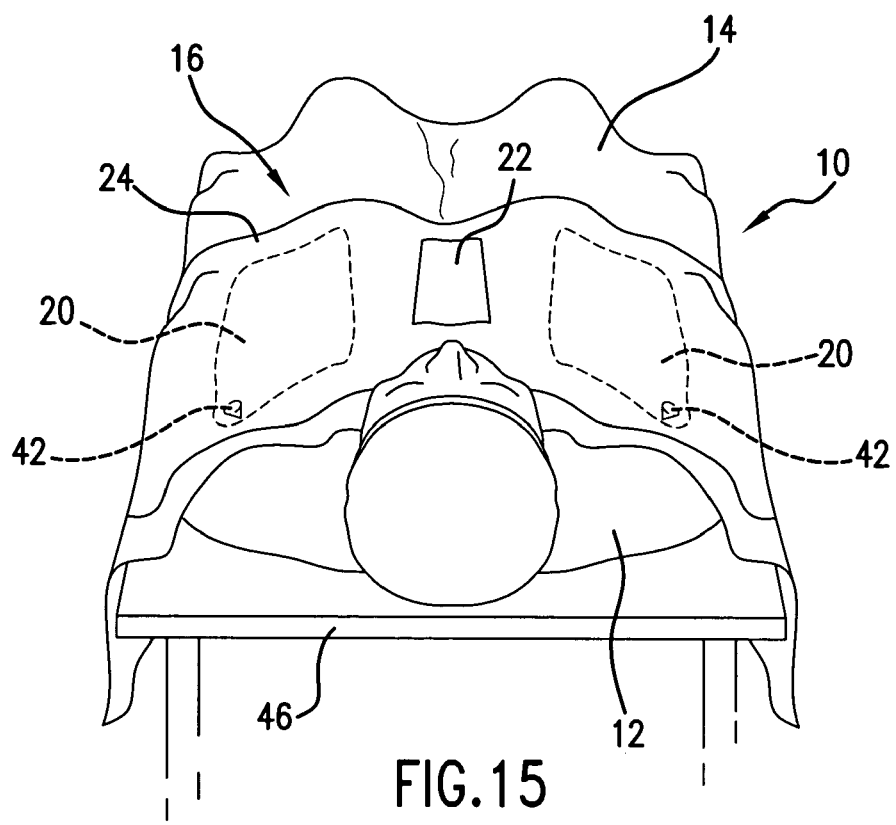
FIG. 15 is a perspective view of an exemplary embodiment of a surgical drape in accordance with the present invention. The expandable member is in the unexpanded orientation.
Figure 16:
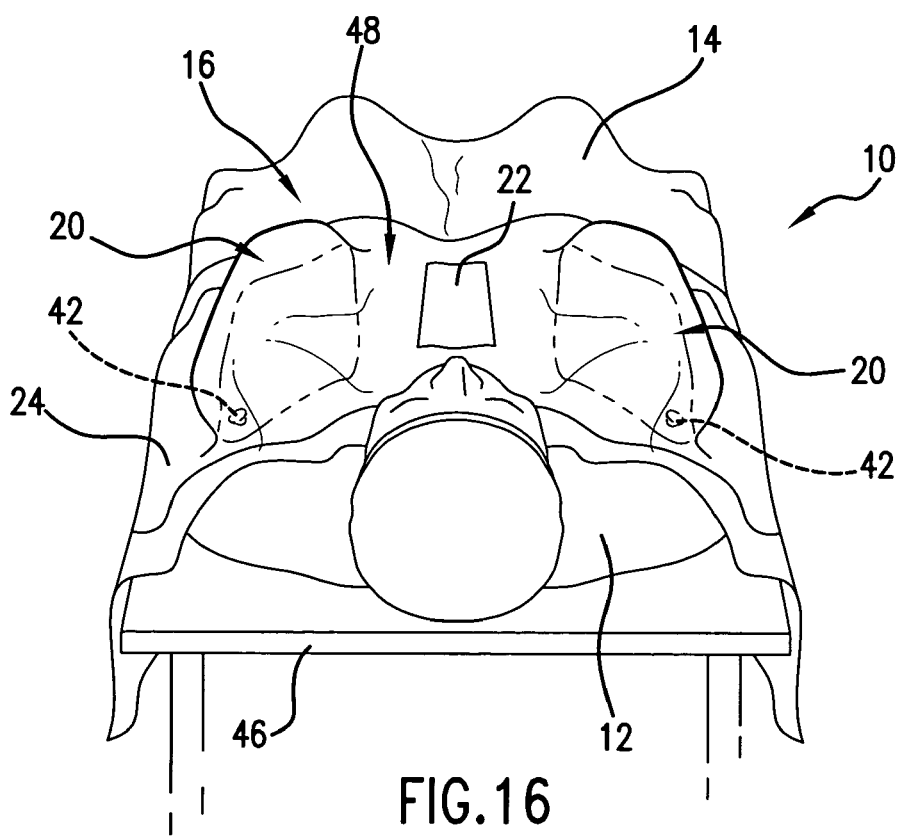
FIG. 16 is a perspective view of the surgical drape of FIG. 15 in which the expandable member is in the expanded orientation.

FIGS. 15 and 16 show the expandable members 20 incorporated into a surgical drape 10 in which the primary purpose of the expandable members 20 is to cushion and protect the patient 12. In this manner, the expandable members 20 are positioned on the sides of the patient 12 and, when expanded, move outward away from the patient 12. It is sometimes the case that the healthcare provider will lean over a table 46 onto which the patient 12 rests in order to conduct a surgical procedure on the patient 12. In these instances, the healthcare provider may inadvertently lean against or contact the patient 12 possibly injuring the patient 12 or disrupting the surgical procedure. The expandable member 20 may thus act as a cushioning barrier to help absorb forces imparted by the healthcare provider should he or she lean against the patient 12.

FIGS. 17 and 18 show the expandable member 20 attached to the sheet 14 and located such that the expandable member 20 is positioned over the legs of the patient 12 when the surgical drape 10 covers a portion of the patient 12. Expansion of the expandable member 20 causes a reorientation of the sheet 14 of the surgical drape 10 as can be seen upon comparison of FIGS. 17 and 18.

Figure 19:
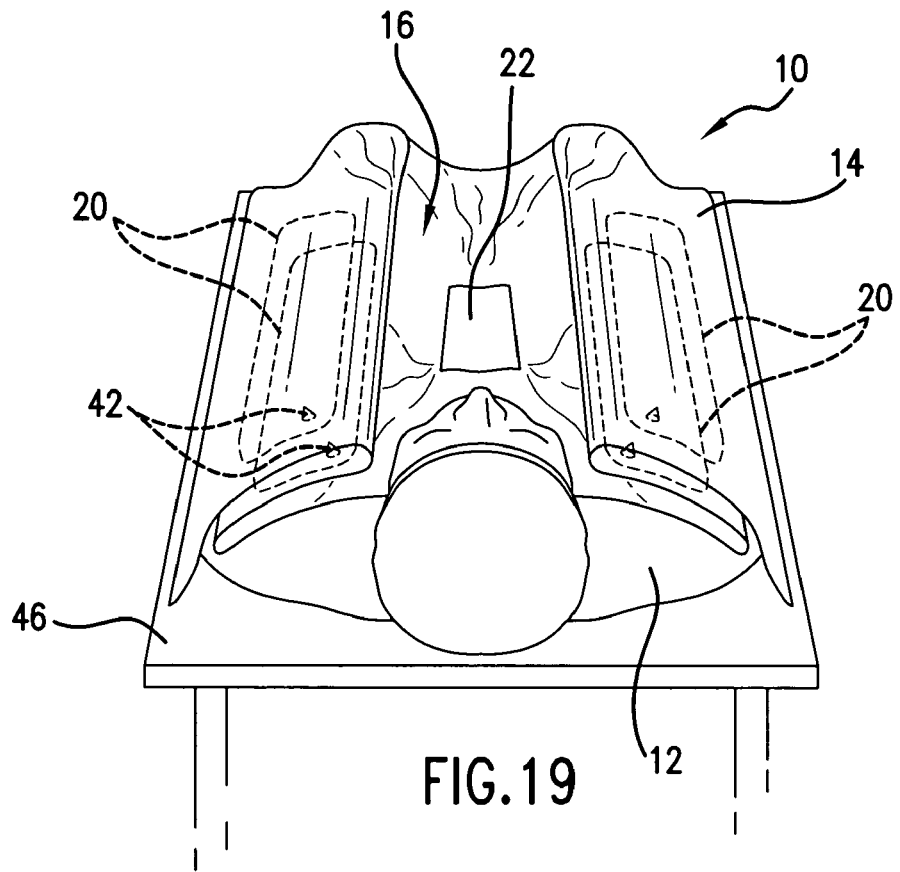
FIG. 19 is a perspective view of an exemplary embodiment of a surgical drape in accordance with the present invention. The expandable member is in the unexpanded orientation.
Figure 20:
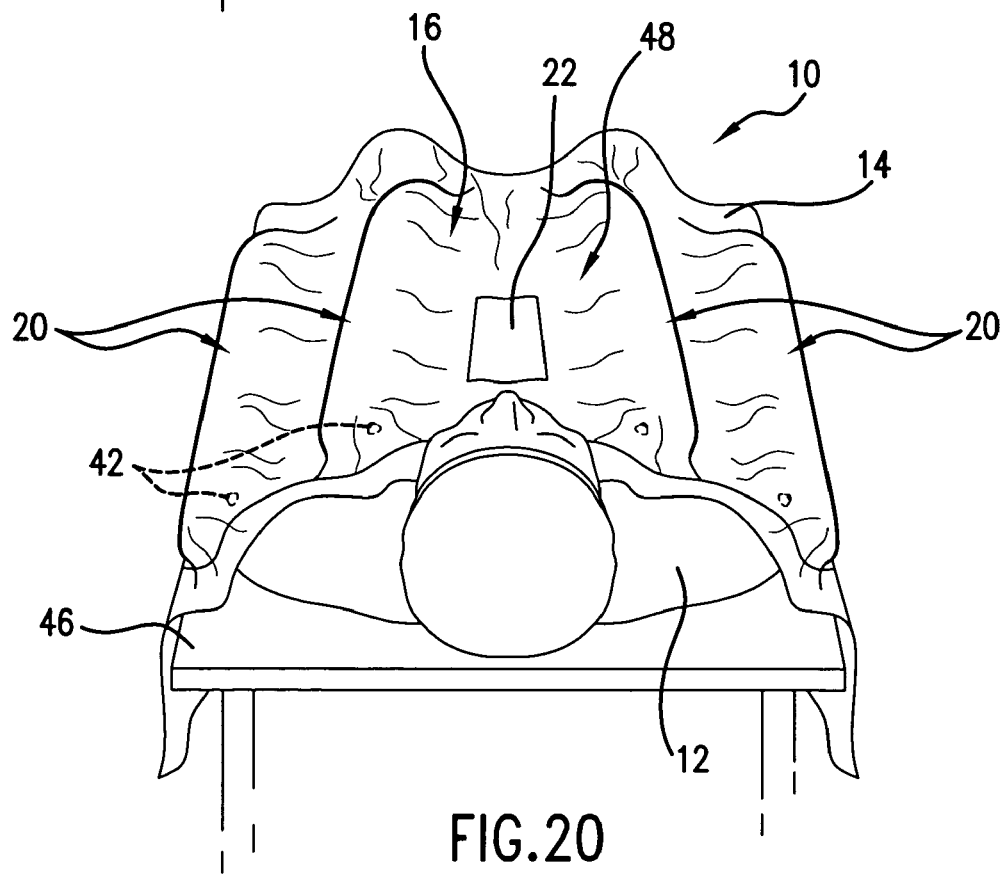
FIG. 20 is a perspective view of the surgical drape of FIG. 19 in which the expandable member is in the expanded orientation.

FIG. 19 shows a surgical drape 10 lying on top of the patient 12 and folded with the expandable members 20 in an unexpanded orientation. The surgical drape 10 may be attached to the patient 12 by adhesive or other securing systems. The expandable members 20 may be expanded in a manner similar to those discussed above. FIG. 20 shows the expandable members 20 in an expanded orientation, which causes the folded portion of surgical drape 10 to unfold on the patient 12 and extend over the table 46 so that the surgical drape 10 is properly positioned into a location allowing for a surgical procedure.

The change in state from the partially folded drape of FIG. 19, before expansion of the expandable members 20, to the completely unfolded drape of FIG. 20 is the result of intentionally using expansion of the expandable members 20 to aid the healthcare provider in preparing the patient 12 for a surgical procedure. Other configurations of the expandable members 20 as part of the surgical drape 10 are conceivable that would change the state from completely folded to completely unfolded via expansion of the expandable members 20, with appropriate placement of the folded surgical drape 10 on the patient 12 understood. Such a change in state from folded to unfolded during expansion of the expandable members 20 occurs without manually unfolding the surgical drape 10 by the healthcare provider. In addition, the surgical drape 10 may be configured so that deflation of the expandable members 20 from the expanded orientation into the unexpanded orientation causes the surgical drape 10 to fold up into a closed orientation. In this instance, the surgical drape 10 may be at least partially rigid and moved along with the expandable members 20 when the expandable members 20 are unexpanded.

When used as a cushioning member, for example as shown in FIG. 10, the expandable member 20 may vary the height of a portion of the top surface 16 between the unexpanded orientation and the expanded orientation from about 7.6 to about 15 cm (3 to about 6 inches). When used to redirect the flow of fluid or to retain fluid on the sheet 14, the expandable member 20 may change the height of a portion of the top surface 16 between the unexpanded orientation and the expanded orientation a distance of less than about 7.6 cm (3 inches). However, these ranges are only provided as examples.

Figure 21:
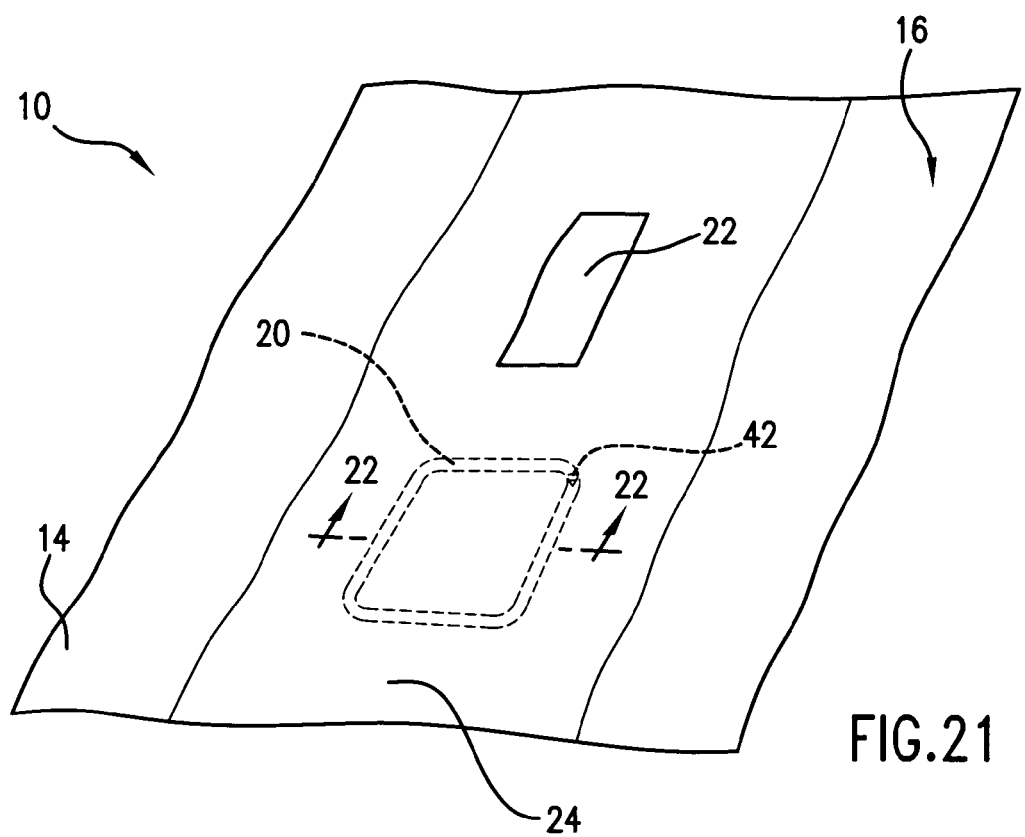
FIG. 21 is a perspective view of an exemplary embodiment of a surgical drape used in accordance with the present invention. The expandable member is in the unexpanded orientation.
Figure 23:
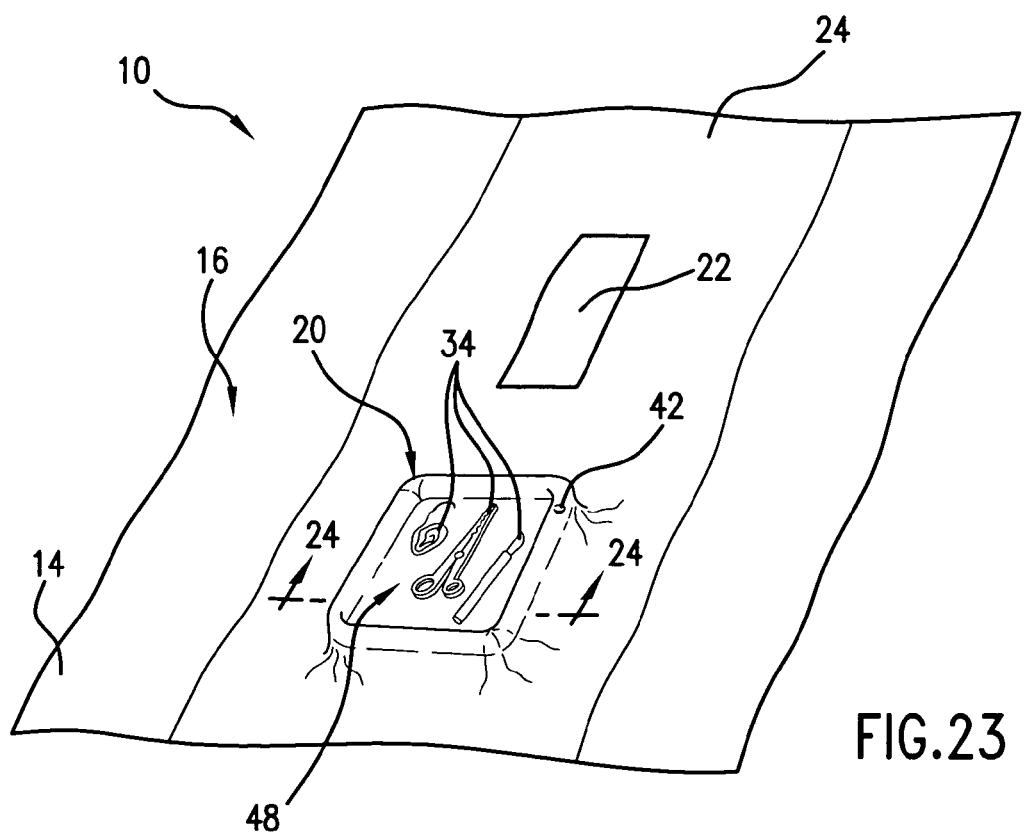
FIG. 23 is a perspective view of the surgical drape of FIG. 21 in which the expandable member is in the expanded orientation.
Figure 22:
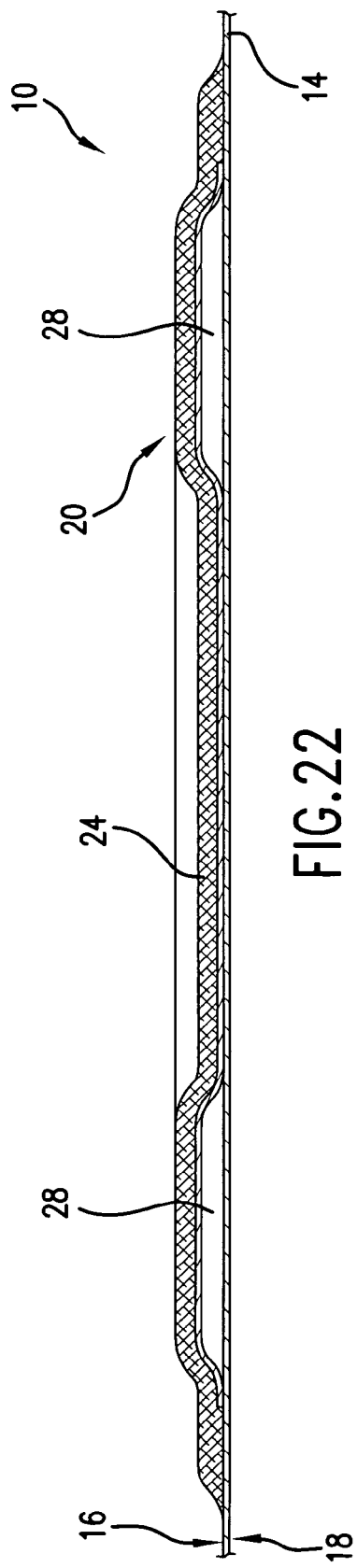
FIG. 22 is a cross-sectional view taken along line 22-22 of FIG. 21.
Figure 24:
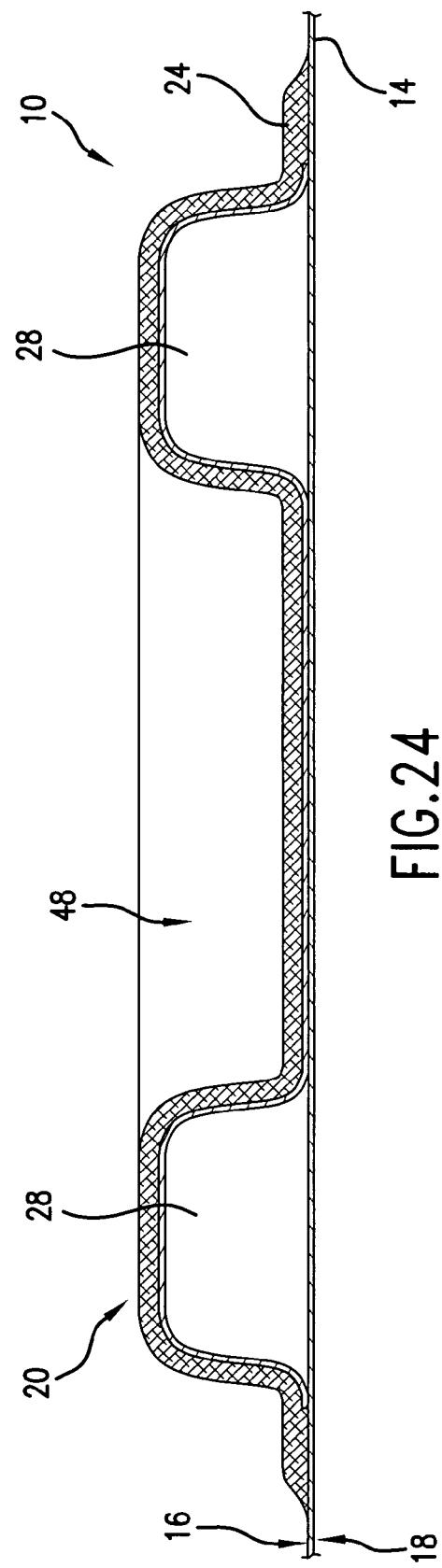
FIG. 24 is a cross-sectional view taken along line 24-24 of FIG. 23.

Another exemplary embodiment of the surgical drape 10 is shown in FIG. 21 though 24. Here, the expandable member 20 is located a distance away from the fenestration 22, and as can be seen in FIG. 22, is positioned underneath the fabric 24 attached to sheet 14. The expandable member 20 is again provided with a port 42 for the introduction of fluid and subsequent expansion. In the expanded orientation, the expandable member 20 forms an instrument holder or a receptacle, on the top surface 16 of the sheet 14. As can be seen in FIG. 23, any manner of surgical instruments 34 may be placed in the valley 48 formed by the expandable member 20 and will be prevented from sliding off of the sheet 14 due to the presence of the expandable member 20. Thus, the healthcare provider need not manipulate any latching mechanism or other fastener in order to retain the surgical instruments 34 on the sheet 14.

When configured to retain the surgical instruments 34, the valley 48 allows for a hands-free passing technique to be employed by the healthcare providers. In this instance, a surgical instrument 34, such as a needle or a sharp, is placed in the valley 48 and is then picked up from the valley 48 by another healthcare provider. In this manner, the surgical instrument 34 is not passed from the hand of one healthcare provider to the hand of another healthcare provider. This technique is effective in reducing the occurrence of percutaneous injury, glove tears, and the contamination of the sterile field during surgery. The valley 48 may be of any shape or size in accordance with various exemplary embodiments of the present invention. For instance, the valley 48 is approximately 3 cm (1.2 inches) in depth in one embodiment.

Figure 25:
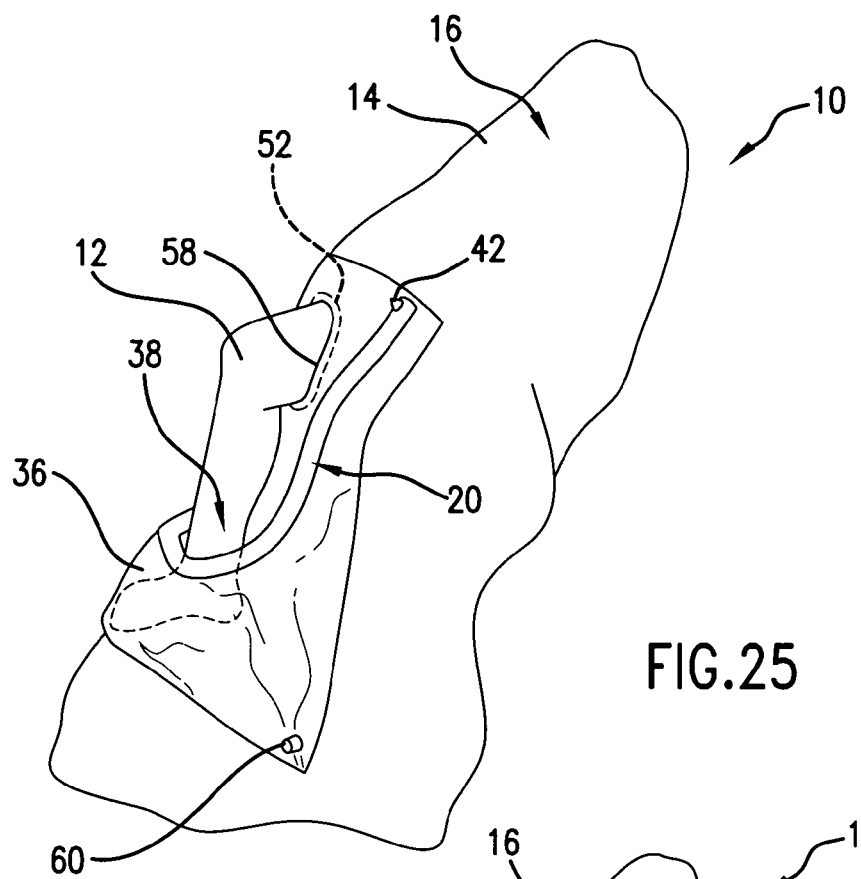
FIG. 25 is a perspective view of a surgical drape that includes a pouch in accordance with one exemplary embodiment of the present invention. The expandable member is in the unexpanded orientation.
Figure 26:
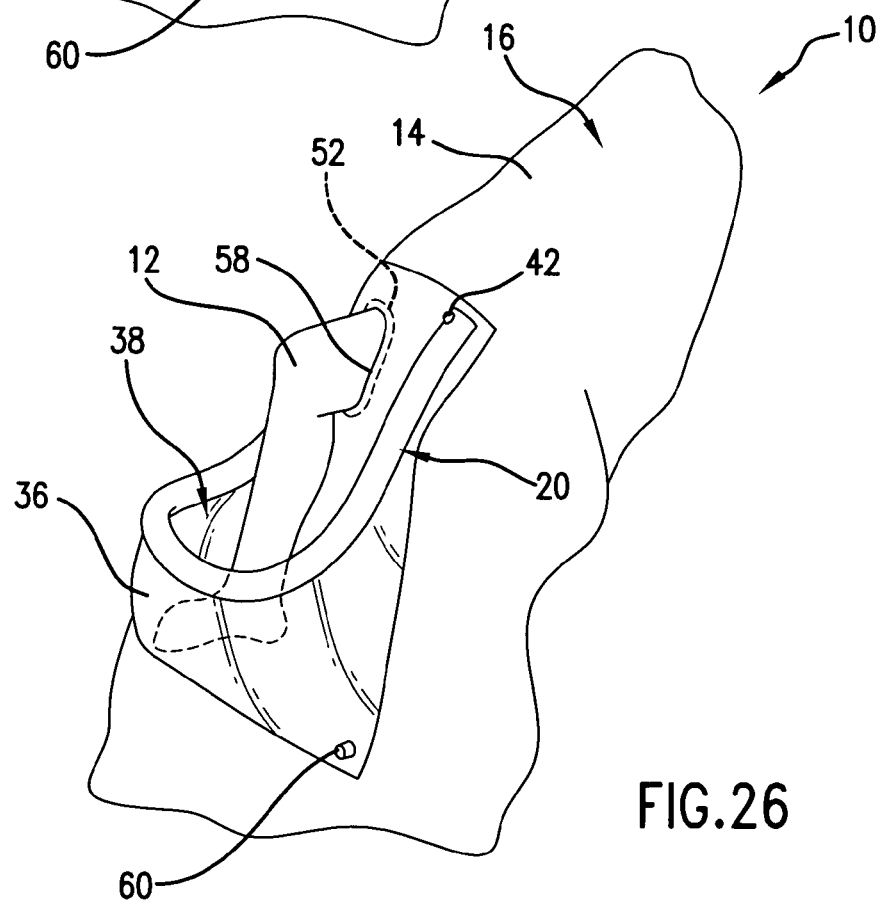
FIG. 26 is a perspective view of the surgical drape of FIG. 25 in which the expandable member is in the expanded orientation.
Figure 27:
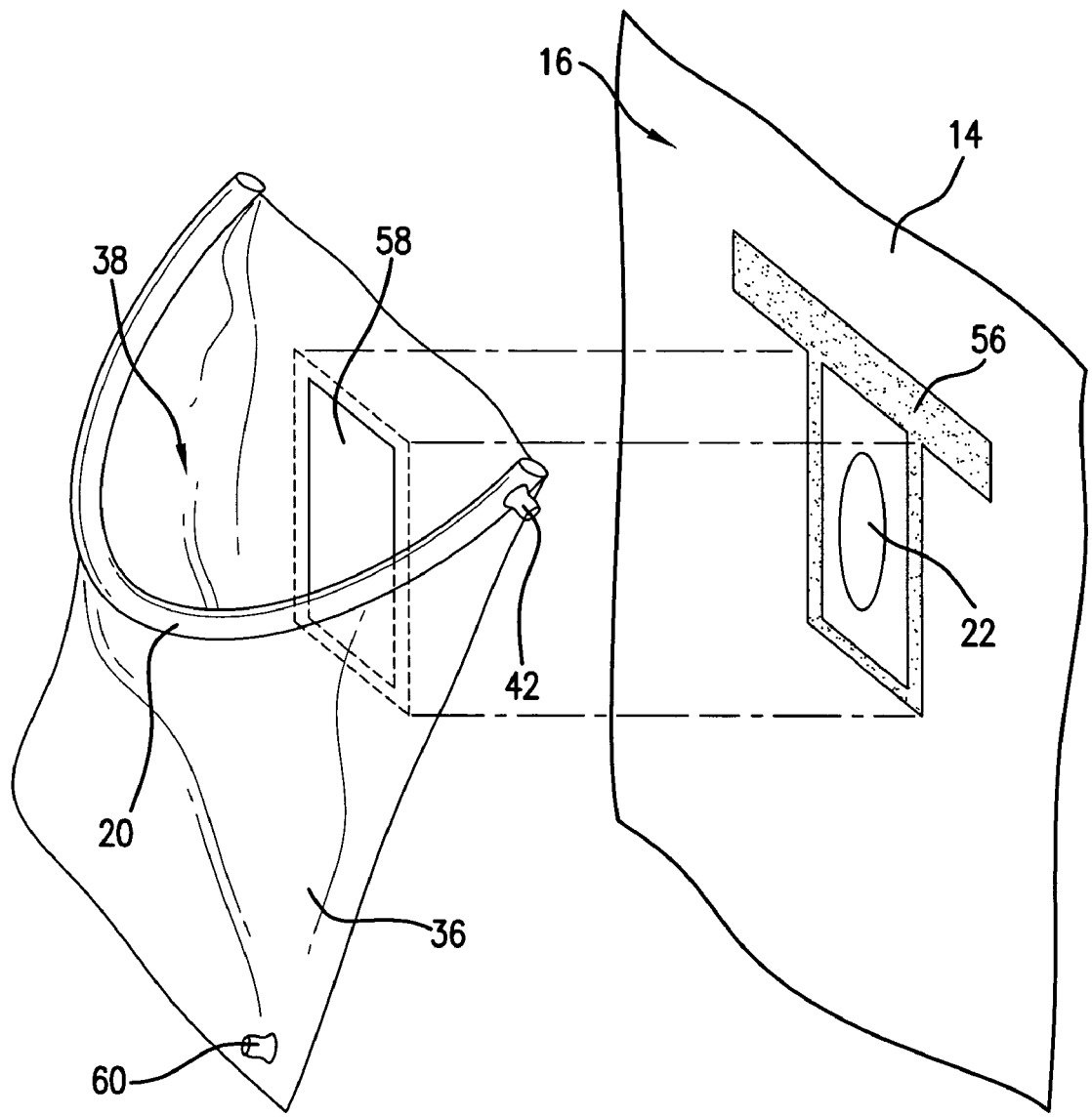
FIG. 27 is an exploded assembly view of the surgical drape that includes a pouch of FIG. 25.

The surgical drape 10 may be provided with a fluid retaining pouch 36 near or around a fenestration 58, as shown in FIGS. 25 through 27, in order to collect and/or retain fluid produced by a surgical procedure. Expandable member 20 is included as part of the fluid retaining pouch 36. The fluid retaining pouch 36 is attached to the surgical drape 10 at least partially by the side portion or an edge immediately adjacent the sheet 14. The attachment between the fluid retaining pouch 36 and the sheet 14 is through a securing system 56, with adhesives or hook and loop elements being non-restrictive examples of such a system 56.

When the expandable member 20 is in the unexpanded orientation, the fluid retaining pouch 36 is essentially closed. Expansion of the expandable member 20 into the expanded orientation as shown in FIG. 26 causes the expandable member 20 to be reoriented such that it moves away from the top surface 16 and helps to define a pronounced inlet opening 38 for the fluid retaining pouch 36. In such an instance, fluid from a surgical procedure may easily be directed through the inlet opening 38 and into the fluid retaining pouch 36. The fluid retaining pouch 36 may be provided with a drainage plug 60 through which fluid contained in the fluid retaining pouch 36 may be removed. Alternatively, the fluid retaining pouch 36 may be filled with fluid until the completion of the surgical procedure, at such time the fluid retaining pouch 36 and/or the sheet 14 may be removed from the table 46 and subsequently disposed.

Although shown in FIG. 26 and FIG. 27 as helping to define the inlet opening 38, it is to be understood that the expandable member 20 may be used in surgical drapes to help define inlet openings other than for fluid retaining pouches 36. Expandable members 20 may also function to define inlet openings into pockets or sleeves for accommodating endoscope components, instruments, tubes, cords, and other items desirable to place in close proximity to the surgical site. When used to define inlet openings for uses other than fluid retaining pouches 36, the expandable members 20 need not be restricted to positions near or around, fenestrations.

It is also to be understood that in accordance with other exemplary embodiments, the use of expandable member 20 for defining inlet openings into pouches, pockets and sleeves attached to surgical drapes 10, may additionally provide other functionality. For instance, in addition to helping define the inlet opening 38, the expandable member 20 may be configured for directing or retaining fluid, providing retention for surgical instruments 34, and/or providing for a cushioning feature on the surgical drape 10. In this regard, a single expandable member 20 may be employed, or multiple expandable members 20 may be employed in the surgical drape 10 to achieve the desired functionality.

To further convey the variety in ways that a surgical drape 10 with the expandable members 20 can be used, nonrestrictive aspects of the fabric 24 and sheet 14 are described. The fabric 24 may be incorporated into the sheet 14 in a variety of manners. For instance, the fabric 24 may be attached using thermal point bonding, ultrasonic point bonding, adhesives, or mechanical bonding. In one exemplary embodiment of the present invention, the fabric 24 is incorporated into the sheet 14 by using an aqueous adhesive, such as an adhesive sold under the name L 8052-01 by Findley Adhesives. The fabric 24 may have the same or different properties as the sheet 14. The fabric 24 may be a multi-layered nonwoven fabric. A film may be incorporated into the fabric 24 and/or sheet 14 in order to inhibit the passage of fluids therethrough. In another instance the fabric 24 may provide structural support in the area surrounding the fenestration 22.

The fabric 24 may be made from nonwoven layers, adhesive layers, film layers, and/or magnetic layers. Some or all of the fabric 24 may be made so as to be hydrophilic or hydrophobic or fluid impervious. Additionally, the fabric 24 may be chemically treated in order to achieve desired absorbency properties. In this manner, some or all of the fabric 24 may be treated with a surfactant in a manner such as that described in U.S. Pat. No. 5,540,979, issued to Yahiaoui, et al., the entire contents of which are incorporated by reference herein in their entirety for all purposes.

The fabric 24 may be made of a meltblown layer that has a spunbond layer positioned on either side. Alternatively, the fabric 24 may be a spunbond-meltblown-film arrangement such as Control® Plus manufactured by Kimberly-Clark located at 1400 Holcomb Bridge Road, Roswell, Ga., 30076-2199. The fabric 24 may include a spunbond layer that is formed from two layers of multicomponent filaments, as described in U.S. Pat. No. 5,418,045 issued to Pike, et al., the entire contents of which are incorporated by reference herein in their entirety for all purposes.

The fabric 24 may be a single nonwoven layer without additional layers, as is suitable when the sheet 14 contains a film to impart fluid barrier attributes, and the fabric 24 needs to only to impart enhanced absorbency. If the fabric 24 is made from a plurality of layers, the layers may be laminated to one another by using conventional techniques known to those skilled in the art. For example, in accordance with one exemplary embodiment one or more meltblown layers may be thermally laminated to one or more spunbond layers using discrete bond points.

It is to be understood that in accordance with various exemplary embodiments of the present invention, the surgical drape 10 need not be provided with the fabric 24. Additionally, in accordance with other exemplary embodiments of the present invention, the sheet 14 does not define the fenestration 22.

In certain exemplary embodiments of the present invention, the expandable member 20 in the expanded orientation does not create a fluid tight seal between the expandable member 20 and an object touching the expandable member 20. As such, the expandable member 20 is configured for allowing some amount of air or other fluid to pass between the expandable member 20 and objects contacting the expandable member 20, for instance the table 46, patient 12, or other portions of the sheet 14. With reference to FIG. 20, the expandable members 20 are configured for allowing air to pass between both the table 46 and the expandable members 20 contacting the table 46, and to allow for air to pass between the patient 12 and the expandable members 20 contacting the patient 12. As such, the expandable members 20 are configured so as to press against an object, but not configured for pressing against an object with sufficient force to create a sealing arrangement. However, in accordance with certain exemplary embodiments, a seal may be created along a portion of the length of the expandable members 20.

With respect to representation of port 42 in the figures it is to be understood that the shape and placement of port 42 serve only as examples and are not restrictive to the types useful in conjunction with the expandable members 20. Nonrestrictive alternatives to port 42 shown in the figures are ports that do not protrude outward from the expandable member 20 or chamber 28 and ports accessed from the top surface of the surgical drape 10.

It should be understood that the present invention includes various modifications that can be made to the surgical drape 10 as described herein that come within the scope of the appended claims and their equivalents.

What is claimed is:

1. A surgical drape for use in overlying a portion of the body of a patient during surgery of the patient, comprising:
   a sheet configured for covering at least a portion of the patient during surgery, the sheet having a top surface and a bottom surface opposite from the top surface and at least a portion of the sheet's bottom surface is configured to be disposed above the patient when in use during surgery, said sheet defining a valley region in said top surface, wherein said sheet defines a fenestration;
   an expandable member carried by the sheet, the expandable member having an unexpanded orientation and an expanded orientation, in the expanded orientation the expandable member forms a raised portion, said expandable member being configured to extend completely around said valley region of said sheet;
   wherein the expandable member completely surrounds the fenestration and is inflated by a fluid from the unexpanded orientation to the expanded orientation.

2. The surgical drape as set forth in claim 1, wherein the expandable member is integrally formed with the sheet.

3. The surgical drape as set forth in claim 1, wherein the expandable member is a separate component from the sheet and is attached to the sheet.

4. The surgical drape as set forth in claim 1, wherein the expandable member is located on the top surface of the sheet.

5. The surgical drape as set forth in claim 1, wherein the expandable member is located on the bottom surface of the sheet.

6. The surgical drape as set forth in claim 1, wherein said sheet defines a fenestration, and further comprising a fabric bordering the fenestration wherein the expandable member is spaced from the fabric.

7. The surgical drape as set forth in claim 1, further comprising a fabric bordering the fenestration wherein the expandable member is carried by the fabric.

8. The surgical drape as set forth in claim 1, further comprising a fluid absorbing fabric contiguous with the sheet.

9. The surgical drape as set forth in claim 1, further comprising a fluid impervious fabric contiguous with the sheet.

10. The surgical drape as set forth in claim 1, further comprising a hydrophobic fabric contiguous with the sheet.

11. The surgical drape as set forth in claim 1, wherein the expandable member is configured to be repeatedly varied between the unexpanded orientation and the expanded orientation.

12. The surgical drape as set forth in claim 1, wherein the expandable member is disposed so that in the expanded orientation the expandable member acts as a cushioning member.

13. The surgical drape as set forth in claim 1, wherein the expandable member is disposed so that in the expanded orientation, the expandable member acts as a diverting member to divert the flow of fluid contacting the sheet.

14. The surgical drape as set forth in claim 1, wherein the expandable member is disposed so that in the expanded orientation, the expandable member acts as a fluid retention member to retain fluid contacting the sheet.

15. The surgical drape as set forth in claim 1, wherein the expandable member is disposed so as to at least partially define a receptacle when in the expanded orientation.

16. The surgical drape as set forth in claim 1, wherein the expandable member comprising an open cell foam reversibly collapsed and constrained in the unexpanded orientation, expands upon being unconstrained into the expanded orientation.

17. The surgical drape as set forth in claim 1, wherein the sheet is in a folded configuration when the expandable member is in the unexpanded orientation, and wherein the sheet unfolds when the expandable member is expanded from the unexpanded orientation to the expanded orientation.

18. The surgical drape as set forth in claim 1, wherein the expandable member is disposed so that in the expanded orientation, the expandable member acts as an instrument holder configured for receiving at least one surgical instrument.

19. The surgical drape as set forth in claim 1, further comprising a pouch carried by the sheet, and wherein in the expanded orientation the expandable member at least partially defines an inlet opening of the pouch.

20. The surgical drape as set forth in claim 1, wherein a plurality of expandable members are present and are configured so as to be separately changed between the unexpanded orientation and the expanded orientation.

21. A surgical drape for use during surgery of a patient, comprising:
a sheet configured for covering at least a portion of the patient during surgery, the sheet having a top surface and a bottom surface opposite from the top surface, the bottom surface configured for facing the patient and the top surface configured for facing away from the patient;
wherein the sheet defines a fenestration through both the top and bottom surfaces of the sheet;
wherein the sheet has a fabric completely bordering the fenestration, the fabric providing for fluid management functionality; and
an expandable member carried by the sheet, wherein the expandable member completely surrounds the fenestration, the expandable member having an unexpanded orientation and an expanded orientation, wherein in the expanded orientation the expandable member forms a raised portion and wherein the expandable member is located on the bottom surface of the sheet.

22. The surgical drape as set forth in claim 21, wherein the expandable member is integrally formed with the sheet.

23. The surgical drape as set forth in claim 21, wherein the expandable member is a separate component from the sheet and is attached to the sheet.

24. The surgical drape as set forth in claim 21, wherein the expandable member is located on the top surface of the sheet.

25. The surgical drape as set forth in claim 21, wherein the expandable member is located between the top and bottom surfaces of the sheet.

26. The surgical drape as set forth in claim 21, wherein the expandable member is spaced from the fabric.

27. The surgical drape as set forth in claim 21, wherein the fabric carries the expandable member.

28. The surgical drape as set forth in claim 21, wherein the fabric is configured to absorb fluid.

29. The surgical drape as set forth in claim 21, wherein the fabric is configured for being fluid impervious.

30. The surgical drape as set forth in claim 21, wherein the expandable member is configured to be repeatedly varied between the unexpanded orientation and the expanded orientation.

31. The surgical drape as set forth in claim 21, wherein the raised portion is disposed to act as a cushioning member to absorb forces imparted onto the surgical drape.

32. The surgical drape as set forth in claim 21, wherein the raised portion is disposed to act as a diverting member to channel the flow of fluid contacting the surgical drape.

33. The surgical drape as set forth in claim 21, wherein the raised portion is disposed to act as a fluid retention member to retain fluid contacting the surgical drape.

34. The surgical drape as set forth in claim 21, wherein the expandable member is disposed so as to at least partially define a receptacle when in the expanded orientation.

35. The surgical drape as set forth in claim 21, further comprising a fluid conveying device configured to be placed into communication with the expandable member, the fluid conveying device configured to provide fluid into the expandable member in order to inflate the expandable member from the unexpanded orientation to the expanded orientation.

36. The surgical drape as set forth in claim 21, wherein the expandable member comprising an open cell foam reversibly collapsed and constrained in the unexpanded orientation, expands upon being unconstrained into the expanded orientation.

37. The surgical drape as set forth in claim 21, wherein the raised member is disposed to act as an instrument holder configured for receiving at least one surgical instrument.

38. The surgical drape as set forth in claim 21, further comprising a pouch carried by the sheet, and wherein in the expanded orientation the expandable member at least partially defines an inlet opening of the pouch.

39. The surgical drape as set forth in claim 21, wherein a plurality of expandable members are present and are configured so as to be separately changed between the unexpanded orientation and the expanded orientation.

40. A surgical drape for use during surgery of a patient, comprising:
- a sheet configured for covering at least a portion of the patient during surgery, the sheet having a top surface and a bottom surface opposite from the top surface, the bottom surface configured for facing the patient and the top surface configured for facing away from the patient;
- wherein the sheet defines a fenestration through both the top and bottom surfaces of the sheet, said fenestration being configured for passage of surgical instruments through the fenestration during performance of surgery on the patient when the patient is disposed beneath the sheet;
- wherein the sheet has a fabric bordering the fenestration, the fabric providing fluid management functionality; and
- an expandable member carried by the sheet, the expandable member completely surrounding the fenestration, the expandable member having a chamber inflatable from an unexpanded orientation to an expanded orientation, the expandable member comprising a port allowing for a fluid to be transferred into the chamber in order to inflate the chamber, wherein in the expanded orientation the expandable member forms a raised portion.

41. The surgical drape as set forth in claim 40, wherein a plurality of expandable members are present and are carried by the sheet.

42. The surgical drape as set forth in claim 40, wherein the sheet has a folded position and an unfolded position, the expanded orientation of the sheet causing at least a portion of the sheet to change positions from the folded position to the unfolded position.

43. The surgical drape as set forth in claim 42, wherein the sheet changes positions from the unfolded position to the folded position when the expandable member changes orientations from the expanded orientation to the expanded orientation.

* * * * *